(12) United States Patent
Tatsuka

(10) Patent No.: US 6,767,700 B2
(45) Date of Patent: *Jul. 27, 2004

(54) TUMOR CELLS HAVING TUMORIGENIC POTENTIAL BUT LACKING INVASIVE/METASTATIC POTENTIAL, METHOD FOR PREPARING THEM AND SCREENING METHOD FOR METASTASIS-RELATED GENES USING THE SAME

(75) Inventor: Masaaki Tatsuka, Hiroshima (JP)

(73) Assignees: Motoharu Seiki, Kanazawa (JP); Chugai Seiyaku Kabushiki Kaisha, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/125,543

(22) PCT Filed: Feb. 26, 1997

(86) PCT No.: PCT/JP97/00554

§ 371 (c)(1),
(2), (4) Date: Aug. 28, 1998

(87) PCT Pub. No.: WO97/32009

PCT Pub. Date: Sep. 4, 1997

(65) Prior Publication Data

US 2001/0006781 A1 Jul. 5, 2001

(30) Foreign Application Priority Data

Feb. 29, 1996 (JP) .............................. 8-69095

(51) Int. Cl.[7] .......................... C12Q 1/68; C12N 15/12; C12N 5/10
(52) U.S. Cl. .......................... 435/6; 435/325; 435/357; 435/354; 435/320.1; 435/455; 536/23.1; 536/23.2; 536/23.5
(58) Field of Search .................. 435/6, 320.1, 325, 435/455, 357, 354; 536/23.1, 23.2, 23.5

(56) References Cited

U.S. PATENT DOCUMENTS 5,792,638 A * 8/1998 Aaronson et al. ........... 435/194

OTHER PUBLICATIONS

Davies et al. Induction of metastatic ability in a stbly diploid benign rat mammary epithelial cell sline by transfection with DNA from human malignant breast carcinoma cell lines. Cancer Res. vol. 54:2785–2793, 1994.*

Kogerman et al. Oncogene–dependent expression of CD44 in Balb/c 3T3 derivatives: correlation with mitastatic competence. Cliln. Exp. Matastasis vol. 14:73–82, 1996.*

Kakunaga et al. Cell variants showing differential susceptibility to ultraviloet light–induced transformation. Science vol. 209:505–507, 1980.*

Induction of the metastatic phenotype by transfection of a benign rat mammary epithelial cell line with the gene for p9Ka, a rat calcium–binding protein, but not with the oncogene EJ–ras–1. Davies et al. Oncogene 8:999–1008, Jun. 1993.*

Secretion of type IV collagenolytic protease and metastatic phenotype: Induction by transfection with c–Ha–ras but not c–Ha–ras plus Ad2–E1a. Garbisa et al. Cancer Research vol. 47:1523–1528, Mar. 1987.*

Identification and quantification of a carcinogen–induced molecular initiation event in cell transformation. Nakazawa et al. Oncogene. vol. 7:2295–2301, Dec. 1992.*

Resistance of murine LTA cells to oncogene—mediated progression from tumorigenic to metastatic phenotype. Tuck et al. Anticancer Research vol. 10:1507–1514, Oct. 1990.*

Genetic manipulation of E–cadherin expression by epithelial tumor cells reveals an invasion suppressor role. Vleminckx et al. Cell. vol. 66:107–119, Jul. 1991.*

Different metastatic potentials of ras– and src– transformed BALB/c 3T3 A31 variant cells. Tatsuka et al. Molecular carcinogenesis. vol. 15:300–308, Mar. 1996.*

Åkerström B. et al. *J. Immunol.* 135:2589–2592, 1984.
Albini A. et al. *Cancer Res.* 47:3239–3245, 1987.
Bernstein S.C. and Weiberg R. *Proc. Natl. Acad. Sci. USA* 82:1726–1730, 1985.
Brodt P., *Cancer Res.* 46:2442–2448, 1986.
Chomczynski P. et al. *Anal. Biochem.* 162:156–169, 1987.
Cooper J.A. et al. *J. Virol.* 48:752–764, 1983.
Dong J.T. et al. *Science* 268:884–886, 1995.
Egan S.E. et al. *Science* 238:202–205, 1987.
Fidler, I.J. et al., *J. Natl. Cancer Inst.* 67:947–956, 1981.
Fidler, I.J. et al., *Am. J. pathol.* 97–633–648, 1979.
Fidler, I.J., *Cancer Res.* 35:218–224, 1975.
Fidler, I.J., *Nature*, 242:148–149, 1973.
Graham F.L. and Van Der EB A.J. "Transformation of Rat Cells by DNA of Human Adenoma 5", *Virology* 54:530–539, 1973.
Gunthert U. et al. *Cell* 65:13–24, 1991.
Habets G.G.M. et al. *Cell* 77:537–549, 1994.

(List continued on next page.)

*Primary Examiner*—David Guzo
(74) *Attorney, Agent, or Firm*—Foley & Lardner

(57) ABSTRACT

Tumor cells having tumorigenic potential but lacking invasive/metastatic potential are established by introducing an oncogene of the ras family into a BALB/c 3T3 A31-variant cell. A screening method for genes having the property of conferring invasive/metastatic potential is also provided, which comprises transfecting DNA derived from a tumor tissue obtained from the surface or inside of a mammal or derived from a tumor cell line into tumor cells having tumorigenic potential but lacking invasive/metastatic potential, isolating cells having acquired invasive/metastatic potential and extracting DNA therefrom.

14 Claims, 5 Drawing Sheets

OTHER PUBLICATIONS

Jamieson S. et al. *Int. J. Cancer* vol. 46 (1990) "Transfection of a non-metastic diploid rat mammary epithelial cell line with the oncogenes for EJ–ras–1 and polyoma large T antigen" pp. 1071–1080.
Jove R. et al. *J. Virol.* 60:849–847, 1986.
Kakanuga T. et al. (eds.) Transformation Assay of Established Cell Lines: Mechanisms and Application, Oxford University Press, New York, 1986, pp. 55–73.
Kakunaga T., in Omen G.S. et al. (eds.) "Genetic Variability in Responses to Chemical Exposure", Cold Spring Harbor Laboratory, New York, 1984, pp. 55–74.
Kakunaga T. et al. *Science* 209:505–507, 1980.
Kanai T. et al. *Jpn. Cancer Res.* 78:1314–1318, 1987.
Kasai M. et al. *Eur. J. Immunol.* 10:175–180, 1980.
Kawaguchi T et al. *Clin. Exp. Metastasis* 10:225–238, 1992.
Kizaka et al. *Mol. Cell. Biol.* 9:5669–5675, 1989.
Laemmli U.K., *Nature* 227:680–685, 1979.
Leone A. et al. *Cell* 65:25–35, 1991.
Maniatis T. et al.. "Molecular Cloning: A Laboratory Manual", Cold Spring Harbor Laboratory, New York, 1982.
Muschel R.J. et al. *Am. J. Pathol.* 121:1–8, 1985.
Olsson L. et al. *Cancer Res.* 41:4706–4709, 1981.
Ota et al., *Clin. Exp. Metastasis* 10:297–308, 1992.
Pál K. et al. *Invasion Metastasis* 5:159–169, 1985.
Poste G. et al. *Proc. Natl. Acad. Sci. USA* 78:6226–6230, 1981.
Talmadge, J.E., et al., *J. Natl. Cancer Inst.* 69:975–980, 1982.
Taniguchi S. et al. *Cancer Res.* 49:6738–6744, 1989.
Taparowsky E. et al. *Nature* 300:762–765, 1982.
Tatsuka M. et al. *Exp. Cell Res.* 185:342–352, 1989.
Tatsuka et al. *Exp. Cell Res.* 178:154–162, 1988.
Thorgeirsson U.P. *Mol. Cell. Biol.* 5:259–262, 1986.
Towbin H. et al. *Proc. Natl. Acad. Sci. USA* 76:4350–4354, 1979.
Wexler H. *J. Natl. Cancer Inst.* 36:641–645, 1996.
Yagi T. et al. *Mol. Carcinog.* 1:222–228, 1989.
Young M.R. et al., *Cancer Res.* 45:3918–3923, 1985.
Armelin H.A. et al., "Neoplastic Transformation of 3T3 Mouse Embryo Cells with c–myc– and c–Ha–ras–1 Oncogenes", *Brazilian J. Med. Biol. Res.*, 21:1155–1161 (1988), Alan R. Liss, Inc.
Zhan X et al., "Growth Factor Requirements of Oncogene–Transformed NIH 3T3 and BALB/c 3T3 Cells Cultured in Defined Media", *Molecular and Cellular Biology*, 6(10):3541–3544 (1986), American Society for Microbiology.
Kovary K. et al., "Glucocorticoid Dexamethasone Reversibly Complements EJ–RAS Oncogene to Transform Mouse Embryo BALB–3T3 Cells", *Journal of Cellular Biochemistry*, 41(4):171–178 (1989), Alan R. Liss, Inc.
Garcia I. et al., "Establishment of Two Rabbit Mammary Epithelial Cell Lines with Distinct Oncogenic Potential and Differentiated Phenotype after Microinjection of Transforming Genes", *Molecular and Cellular Biology*, 6(6):1974–1982 (1986), Alan R. Liss, Inc.
Tatsuka M. et al., "A BALB/c 3T3–Transformed Cell Lien Suitable for Transfection Assay of Metastasis–Inducing Genes", *Int. J. Cancer*, 71(1): 88–93 (1997), Wiley–Liss, Inc., USA.
Davies B. et al., "Induction of Metastatic Ability in a Stably Benign Rat Mammary Epithelial Cell Line by Transfection with DNA from Human Malignant Breast Carcinoma Cell Lines", *Cancer Research*, 54:2785–2793, (1994).
Boylan J.F. et al., "Role of the Ha–ras ($Ras^H$) Oncogene in Mediating Progression of the Tumor Cell Phenotype (Review)", *Anticancer Research*, 10(3):717–724 (1990).
Tatsuka M. et al., "Elongation factor–1α gene determines susceptibility to transformation", *Nature*, 359(6393):333–336 (1992).

* cited by examiner

Fig. 1

| Cell line | Amount of DNA applied 5  10  15 (μg) | Relative increment of copy number |
|---|---|---|
| 1-1 | | - |
| 1-1ras | | 1 |
| 1-1ras1000 | | 16 |
| 1-13 | | - |
| 1-13ras | | 1 |
| 1-13ras1000 | | 4 |

Fig. 3
A
1 2 3 4 5 6 7 8 9 10
p60<sup>src</sup> ▶
B
1 2 3 4 5 6 7 8 9 10
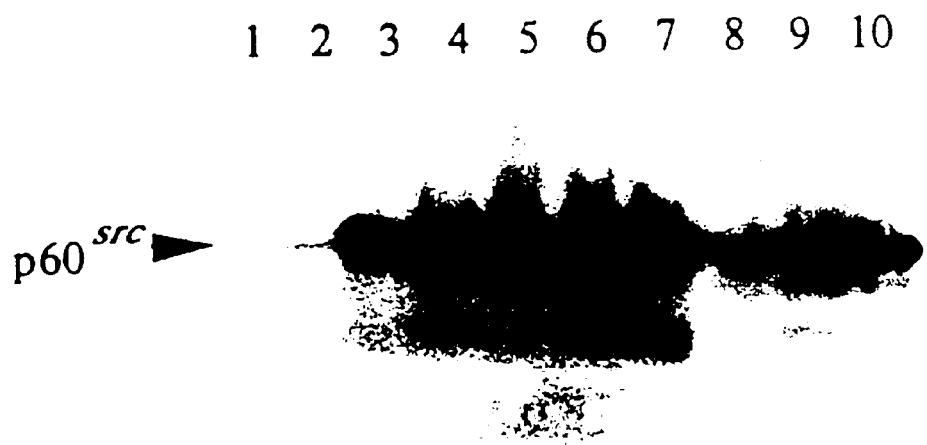
p60<sup>src</sup> ▶

TUMOR CELLS HAVING TUMORIGENIC POTENTIAL BUT LACKING INVASIVE/METASTATIC POTENTIAL, METHOD FOR PREPARING THEM AND SCREENING METHOD FOR METASTASIS-RELATED GENES USING THE SAME

FIELD OF THE INVENTION

The present invention relates to tumor cells having tumorigenic potential but lacking invasive/metastatic potential, a method for preparing them and a screening method for metastasis-related genes using them.

PRIOR ART

Invasion and metastasis occur at the final stage of tumor progression and are the major cause of death of cancer patients. However, it is difficult to treat such effects because the molecular mechanism by which malignant phenotypes of tumor cells such as invasion/metastasis are expressed has been mostly unknown. Although the expression of malignant phenotypes such as invasion/metastasis has long been recognized as a biological phenomenon which is pathologically distinguished from tumor formation in carcinogenic process, there has been only limited information about biochemical basis therefor and target groups of molecules for therapy have not been well identified.

Generally, accumulation of alterations of genetic information of oncogenes and tumor suppressor genes is thought to make cells cancerous and sometimes invasive/metastatic. Namely, a gene that plays a role in mediating an external signal into the nucleus is mutated to form a gene product, which activates the downstream signaling cascade continuously. This causes phenotypes of tumor cells to be expressed. It is also thought that tumor cells become invasive/metastatic during tumor progression as a result of additional genetic alterations to those required for tumorigenicity (Evans C. W. The Metastatic Cell: Behavior and Biochemistry, Chapman & Hall, London, 1991). Therefore, metastasis of tumor cells may be induced by an aberrant intracellular signaling system that is different from the signaling system required for tumor-igenicity. Thus, it is very important for investigations of the mechanism of invasion/metastasis to elucidate a metastasis-specific tumor-related signaling pathway that is responsible for tumor cells becoming invasive/metastatic.

For such investigations, a cell which could separably acquire tumorigenic potential and invasive/metastatic potential by oncogene transfer would be useful for identifying the above pathway and molecules involved therein.

A set of two cells derived from the same parent strain, one of which has tumorigenic potential but lacks invasive/metastatic potential while the other has both potentials, would be useful for investigating the signaling pathway involved in metastasis. Some tumor cell lines satisfying this criterion have already been established. They include rodent-derived cell lines K1735, B16, T-lymphoma L5178Y, Lewis lung carcinoma and rat ascites hepatoma AH7974, as well as their derivatives obtained by in vitro culture and selection of cells recovered from in vivo metastases of these cell lines (Fidler I. J. et al., J. Natl. Cancer Inst. 67:947–956, 1981; Talmadge J. E. et al., J. Natl. Cancer Inst. 69:975–980, 1982; Fidler I. J., Nature 242:148–149, 1973; Fidler I. J., Cancer Res. 35:218–224, 1975; Fidler I. J. et al., Am. J. Pathol. 97:633–648, 1979; Ota et al., Clin. Exp. Metastasis 10:297–308, 1992; Olsson L. et al., Cancer Res. 41:4706–4709, 1981; Brodt P., Cancer Res. 46:2442–2448, 1986; Pal. K. et al., Invasion Metastasis 5:159–169, 1985; Young M. R. et al., Cancer Res. 45:3918–3923, 1985; Kawaguchi T. et al., Clin. Exp. Metastasis 10:225–238, 1992). However, phenotypes of these cell lines are sometimes unstable during experimentations (Poste G. et al., Proc. Natl. Acad. Sci. USA 78:6226–6230, 1981) and many properties of these cell lines that are not related to the acquisition of invasive/metastatic potential may change during in vivo selection.

It would be useful and valuable if a stable set of cell lines as described above could be obtained by oncogene transfer. However, whether or not cells acquire tumorigenic potential and invasive/metastatic potential by oncogene transfer depends on the nature of the cell line used (Muschel R. J. et al., Am. J. Pathol. 121:1–8, 1985). Moreover, oncogene transfer frequently induces invasive/metastatic potential in recipient cells to a greater or lesser extent simultaneously with tumorigenicity (Thorgeirsson U. P., Mol. Cell. Biol. 5:259–262, 1985; Egan S. E. et al., Science 238:202–205, 1987). Up to the present, no report has shown exact establishment of a cell line having tumorigenic potential but lacking invasive/metastatic potential and a cell line having both of these potentials. Thus, it was not easy to separately use characteristics of tumorigenic potential and invasive/metastatic potential of tumor cells for investigations in an experimental system.

It is an object of the present invention to establish a tumor cell line having tumorigenic potential but lacking invasive/metastatic potential, which is suitable for investigating the difference between the signaling pathway for acquiring tumorigenic potential and the signaling pathway for acquiring invasive/metastatic potential. Such a tumor cell line can be used in combination with a cell line derived from the same parent strain but having both of tumorigenic and invasive/metastatic potentials for investigations of characteristics of invasive/metastatic potential. It is another object of the present invention to develop a screening method for tumor metastasis-related genes using the tumor cell line of the present invention.

SUMMARY OF THE INVENTION

As a result of careful studies to overcome the above problems, we succeeded in establishing a tumor cell line having tumorigenic potential but lacking invasive/metastatic potential by introducing a specific oncogene into a recipient cell.

Accordingly, the present invention provides a tumor cell having tumorigenic potential but lacking invasive/metastatic potential. A preferred tumor cell of the present invention having such properties is 1-1ras1000 deposited with the National Institute of Bioscience and Human-Technology of the Agency of Industrial Science and Technology under accession number FERM BP-5406.

The deposit was made on Feb. 20, 1996 and the address of the National Institute of Bioscience and Human Technology Agency of Industrial Science and Technology, Ministry of International Trade and Industry, is 1-3, Higashi 1-chome, Tsukuba-shi, Ibaraki-ken 305, Japan.

The present invention also provides a method for preparing said tumor cell having tumorigenic potential but lacking invasive/metastatic potential by introducing an oncogene of the ras family into a BALB/c 3T3 A31 variant cell.

The present invention also provides a screening method for genes having the property of conferring invasive/metastatic potential, which comprises transfecting DNA derived from a tumor tissue obtained from the surface or inside of a mammal or derived from a tumor cell line into a tumor cell having tumorigenic potential but lacking invasive/metastatic potential, isolating cells having acquired invasive/metastatic potential and extracting DNA therefrom.

BRIEF DESCRIPTION OF THE DRAWINGS

FIG. 1. The copy number of introduced mutated c-Ha-ras gene by slot blot hybridization in ras-transformed A31 variant cells (electrophoretic photographs).

FIG. 3. (Parts A–B) Immunoblotting analysis (A) and phosphorylation assay (B) of v-src-transformed BALB/c 3T3 A31 variant cells (electrophoretic photographs). Lane 1: 1-1; Lane 2:1-13; Lanes 3–6:1-1-derived src-transformants; Lanes 7–10:1-13-derived src-transformants.

DETAILED DESCRIPTION OF THE INVENTION

Figure 2:
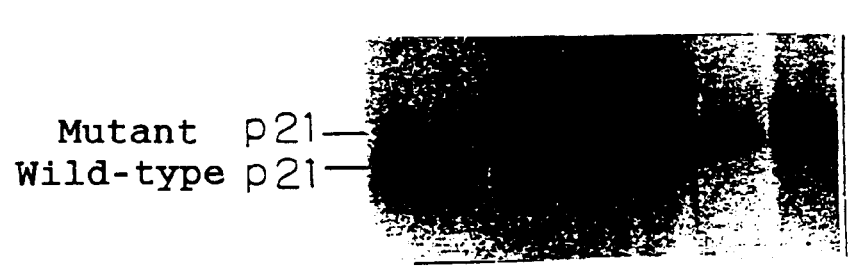
FIG. 2. Immunoblotting analysis of ras-transformed A31 variant cells using an anti-p21$^{ras}$ monoclonal antibody NCC-RAS-004 (electrophoretic photographs). Lane 1:5 ng of standard protein p21Gly-12 corresponding to the product of normal human c-Ha-ras1 plus 5 μl of lysate from T24 bladder carcinoma cells carrying mutated c-Ha-ras1 gene; Lane 2:5 μl of lysate from A31-1-1 cells: Lane 3:50 μl (10-fold excess) of lysate from A31-1-13 cells; Lane 4:5 μl of lysate from A31-1-1ras cells; Lane 5:5 μl of lysate from 1-1ras1000 cells; Lane 6:5 μl of lysate from A31-1-13 cells; Lane 7:5 μl of lysate from 1-13ras1000 cells.

Suitable recipient cells for preparing a cell line having tumorigenic potential but lacking invasive/metastatic potential may preferably be selected so that the resulting cell line can be used to prepare a counterpart of the above set of cell lines, i.e. a cell line having both of tumorigenic potential and invasive/metastatic potential. In this respect, suitable recipient cells for oncogene transfer should have the following properties:

1) they should have a stable non-metastatic phenotype;
2) they should be able to afford a cell which has acquired invasive/metastatic potential by oncogene transfer;
3) they should be able to select a cell which has acquired invasive/metastatic potential by oncogene transfer.

Recipient cells satisfying these properties include but are not limited to, for example, BALB/c 3T3 A31 cells (Kakunaga T., et al. (eds.) Transformation Assay of Established Cell Lines: Mechanisms and Application, Oxford University Press, New York, 1985, pp. 55–73), and other cells having the above properties. BALB/c 3T3 A31 cells include, for example, BALB/c 3T3 A31-1-1, BALB/c 3T3 A31-1-8 and BALB/c 3T3 A31-1-13 established by Kakunaga as used in the examples of the present invention (Kakunaga et al., Science 209:505–507, 1980).

The oncogene to be introduced into a recipient cell may be an oncogene which allows the recipient cell to form a focus (focus formation or a swell of cells means cancerization of cells) and has the activity of conferring no invasive/metastatic potential, such as a gene of the ras family. According to the present invention, tumor cells having tumorigenic potential but lacking invasive/metastatic potential could be established particularly by using, but not limited to, the activated c-Ha-ras.

Tumor cells of the present invention are prepared by providing a plasmid carrying said oncogene and introducing it into a recipient cell. A convenient method for introducing an oncogene into a recipient cell is electroporation (Tatsuka et al., Exp. Cell Res. 178:154–162, 1988), but other means such as the calcium phosphate method, microinjection may also be used.

Transformed cells are seeded in dishes to assay focus formation, and arising transformed foci are isolated and multiplied as an independent cell strain or pooled.

Correct integration of the oncogene in the transformed cells can be ascertained by Southern blot analysis, while transcription of the integrated gene into mRNA can be ascertained by Northern blot analysis of the transcribed mRNA. Furthermore, translation of mRNA into protein can be ascertained by immunoblotting analysis using, for example, an anti-p21$^{ras}$ antibody.

An animal is used to evaluate tumorigenic potential and invasive/metastatic potential of thus obtained cell line. In the present invention, BALB/c nude mice were used. In tumorigenicity assay, transformed cells were subcutaneously injected into the nude mice to observe whether or not a tumor is formed, and growth rate and latency period (the period from injection to detection of a tumorous nodule). In experimental metastasis assay, transformed cells were injected into the tail vein of the nude mice, and after 5 weeks, the mice were sacrificed and autopsied for metastasis.

The present invention thus succeeded in establishing cell lines having tumorigenic potential but lacking invasive/metastatic potential as described above. A particularly preferable cell line established by the present invention was designated as 1-1ras1000 and internationally deposited with the National Institute of Bioscience and Human-Technology of the Agency of Industrial Science and Technology (residing at 1-3, Higashi 1-Chome, Tsukuba-city, Ibaraki-prefecture, 305 Japan) on Feb. 20, 1996 under accession number FERM BP-5406. 1-13ras1000 is another preferable tumor cell line having similar properties to those of 1-1ras1000.

1-1ras1000 is a clone obtained by amplification to enhance the expression level of the oncogene introduced, in which the ras gene is overexpressed at about 16-fold amplification of the parent strain isolated from foci. The non-metastatic phenotype of 1-1ras1000 cells is so stable that they can not be turned metastatic even after in vitro passage or treatment with initiators such as UV rays or methylcholanthrene or treatment with TPA. It is very difficult to obtain an invasive/metastatic clone from these cells by selection involving permeation through micropore filters coated with basement membrane (MATRIGEL). MATRIGEL is a basement membrane matrix extracted from the Engelbreth-Holm-Swarm mouse tumor and is rich in basement membrane proteins. The major matrix components are laminin, collagen IV, entactin, and heparan sulfate proteoglycan (perlecan); the matrix also contains growth factors, matrix metalloproteinases and other proteinases.

Thus, 1-1ras1000 cells have a very stable non-metastatic phenotype without expressing metastatic phenotype. However, it is possible that this property may result from potential lack of invasive/metastatic potential in 1-1ras1000 cells. The src oncogene introduced into these cells induced a great number of metastases in lung. This proved that 1-1ras1000 cells do not lack the step of acquiring invasive/metastatic potential. The cells that took up invasive/metastatic src showed a higher motility than the cells that took up ras on basement membrane (MATRIGEL). Also in experiments using micropore filters, src-transformed cells were invasive for basement membrane.

The present invention thus provides a set of a tumor cell line having tumorigenic potential but lacking invasive/metastatic potential and a tumor cell line having both of tumorigenic potential and invasive/metastatic potential as described above, allowing characteristics of invasive/metastatic potential and tumorigenic potential to be separately used for investigations.

Cell lines having tumorigenic potential but lacking invasive/metastatic potential of the present invention can be used for screening for genes conferring invasive/metastatic potential. The screening method for genes having the property of conferring invasive/metastatic potential according to the present invention can be performed by transfecting DNA derived from a tumor tissue obtained from the surface or inside of a mammal or derived from a tumor cell line into a cell line of the present invention, isolating cells having acquired invasive/metastatic potential and extracting DNA therefrom.

A specific example of the screening method for genes having the property of conferring invasive/metastatic potential using strain 1-1ras1000 of the present invention can be performed by the following procedures:

1) Prepare a genomic gene of a metastatic tumor cell (derived from a tumor tissue obtained from the surface or inside of a mammal or derived from a tumor cell line) or a cDNA library (derived from a tumor tissue obtained from the surface or inside of a mammal or derived from a tumor cell line) constructed with a mammalian cell expression vector.
2) Introduce either the genomic gene or cDNA library obtained in 1) and a selectable marker (for example, a hygromycin-resistant gene) into 1-1ras1000 cells, by using the calcium phosphate method, electroporation, lipofection or the like. Other selecting means such as neo-resistant genes or gpt selection may also be used.
3) If the selectable marker is a hygromycin-resistant gene, grow the cells in a medium containing hygromycin to afford hygromycin-resistant cells.
4) Select hygromycin-resistant cells on the basis of invasive/metastatic potential.
5) Recover non-c-Ha-ras gene fragments containing human gene-specific Alu repeats by using, for example, plaque hybridization.

If a cDNA library prepared with a mammalian cell expression vector was introduced, gene fragments can be recovered as episomes (Tatsuka M. et al., Nature 359:333–336, 1992) or using plasmid rescue, PCR or library construction.

6) Introduce thus recovered gene fragments alone or in mixture into 1-1ras1000 cells and examine invasive/metastatic potential. Specifically, for example, phage DNA obtained by plaque hybridization may be multiplied for each clone and transfected alone or in mixture into 1-1ras1000 cells, and the transfected cells may be injected subcutaneously or into the tail vein of nude mice to obtain a phage clone harboring metastatic cells.
7) Isolate nearly full-length CDNA from the CDNA library using a gene conferring invasive/metastatic potential as a probe and determine its nucleotide sequence. Determine the amino acid sequence on this basis.
8) Screen a human genomic gene library using the cDNA isolated in 7) as a probe to isolate human genomic genes containing all the exons.
9) Integrate the cDNA isolated in 7) into a mammalian cell expression vector and transfect it into 1-1ras1000 cells to examine invasive/metastatic potential.

Thus obtained genes can be regarded as genes conferring invasive/metastatic potential on tumor cells.

Various studies have previously been devoted to screening for metastasis-related genes. For example, Weiberg's group tried expression cloning of a metastatic gene using NIH3T3 cells with failure (Bernstein S. C. and Weiberg R., Proc. Natl. Acad. Sci. USA 82:1726–1730, 1985). Genes such as nm23 (Leone A. et al., Cell 65:25–35, 1991), CD44 (Gunthert U. et al., Cell 65:13–24, 1991), Kai-1 (Dong J. T. et al., Science 268:884–886, 1995) have been cloned by a process involving extracting mRNA from highly metastatic tumor cells while separately extracting mRNA from less metastatic tumor cells and comparing both mRNAs to identify mRNA prevailing in highly metastatic tumor cells. Alternatively, an potential metastasis gene (Tiam-1) has been cloned by virus-insertion mutagenesis (Habets G. G. M. et al., Cell 77:537–549, 1994). However, many of genes isolated by such processes were not metastasis-related genes, indicating that the efficiency of screening for metastasis-related genes is still low.

If a gene derived from a tumor cell could be introduced into 1-1ras1000 cells of the present invention having tumorigenic potential but lacking invasive/metastatic potential to confer invasive/metastatic potential on said cells, the introduced gene would greatly contribute to the acquisition of invasive/metastatic potential. The above screening method of the present invention can be used to efficiently identify a gene conferring invasive/metastatic potential on tumor cells, and therefore, it is very useful for investigating the mechanism of metastasis.

In the present invention, the v-src oncogene was actually introduced into 1-1ras1000 cells to confirm that these cells have acquired invasive/metastatic potential. Also v-src conferred invasive/metastatic potential on the parent strain BALB/c 3T3 A31. These facts suggest that the src gene is involved in conferring invasive/metastatic potential.

Further in the present invention, DNA was extracted from tumor cell lines having various metastatic potentials and transfected into non-metastatic 1-1ras1000 cells of the present invention, and the transformed cells were injected into nude mice to evaluate metastatic potential. As a result, the transformed cells were found to have acquired metastatic potential, which was stable and unchanged even after subcultures. This demonstrated that 1-1ras1000 cells constitute a valuable screening tool for DNA having tumor metastatic potential.

Thus, the present invention also provides a set of a tumor cell line having tumorigenic potential but lacking invasive/metastatic potential and a tumor cell line derived from the same parent strain and having both of tumorigenic potential and invasive/metastatic potential, which are very useful for investigating the difference between the signaling pathway for acquiring tumorigenic potential and the signaling pathway for acquiring invasive/metastatic potential.

The screening method of the present invention can be used to discriminate benign tumors from malignant tumors, predict the aggressiveness of metastasis or predict organ-specific metastasis. Moreover, genes identified as conferring invasive/metastatic potential on tumor cells by the screening method of the present invention can be used to obtain metastasis-related proteins that are promising for developing novel diagnostic agents or therapeutic agents for tumors. The present invention has a very wide industrial applicability.

The following examples further explain the present invention in detail, but are not construed as limiting the scope thereof.

EXAMPLES

Strains and plasmids used in the examples of the present invention are at first briefly described below.

Strains

BALB/c 3T3 A31-derived clones 1-1 and 1-13 used as recipient cells in the present invention were established by Kakunaga (Kakunaga T. et al., Science 209:505–507, 1980), and are differentially susceptible to radiations—and chemicals—induced neoplastic transformation. Here, early subcultures of the original cell stock were used. UV—and MCA (3-methylcholanthrene)—induced transformants (Tatsuka M., Nature 359:333–336, 1992) and Ki-MSV (Kirsten murine sarcoma virus)—transformed cells (Kakunaga T., in Omen G. S. et al., (eds.), Genetic Variability in Responses to Chemical Exposure, Cold Spring Harbor Laboratory, New York, 1984, pp. 257–274) were also used. All of those transformants were tested to be tumorigenic when subcutaneously injected into nude mice. The negative and positive control cells used in experiments for assessing invasive/metastatic potential were 3Y1 and fos-SR-3Y1-202, respectively (Taniguchi S. et al., Cancer Res. 49:6738–6744, 1989).

All the strains were cultured in EMEM supplemented with 10% FCS in 5% $CO_2$ at 37° C.

Plasmids pSV2neo-ras contains the activated c-Ha-ras inserted into the BamHI site of pSV2neo. pcDsrc contains the v-src oncogene inserted into the EcoRI site of pcDsrc (Yagi T. et al., Mol. Carcinog. 1:222–228, 1989; Kizaka et al., Mol. Cell. Biol. 9:5669–5675, 1989). The plasmid pHyg carrying a hygromycin-resistant gene was also used.

Example 1

Transformation of BALB/c 3T3 A31 Variant Cells

BALB/c 3T3 A31 variant cells established by Kakunaga, clone 1-1 (hereinafter sometimes referred to as A31-1-1) and clone 1-13 (hereinafter sometimes referred to as A31-1-13), were examined for their susceptibility to in vitro transformation induced by UV-irradiation, MCA-exposure and Ki-MSV carrying the v-Ki-ras oncogene as described above.

Focus-Forming Ability of Transformants

A31-1-13 was more susceptible to the chemically and physically induced neoplastic transformation than A31-1-1, as previously reported (Tatsuka M. et al., supra. 1992). Both clones showed similar susceptibility to the Ki-MSV-induced transformation, as previously reported (Kakunaga T., supra. 1984). Morphology of the foci differed between both clones but not with the carcinogens for the induced transformation. The foci were larger and more aggressive in A31-1-13 than in A31-1-1.

Tumorigenicity and Invasive or Metastatic Potential of Transformants

All the transformants were tested to form tumors when subcutaneously injected into nude mice or newborn BALB/c mice while no tumor was formed with the parental cells and Mock transfected cells (for example, cells transformed in the absence of only MCA). Growth rate and latency period did not differ significantly between both clones.

Since activated ras oncogenes are known to often induce invasive/metastatic potential in transformed cells, the transformants carrying an activated ras oncogene were injected into the tail vein of nude mice to examine whether they form metastatic lesions in lung.

Throughout the present invention, tumorigenicity and experimental metastasis assays were performed in the following manner.

BALB/c nude mice at 6–7 weeks of age were provided. Cells were collected after trypsinization and washed with PBS. For tumorigenicity assay, $10^6$ cells were injected subcutaneously into the nude mice. For experimental metastasis assay, $5 \times 10^5$ cells were injected into the tail vein of 7–8 week-old nude mice. The mice injected with ras-transformed cells were sacrificed after 5 weeks and autopsied for metastases. However, preliminary experiments had showed that mice injected with src-transformed cells die in 18–24 days as a result of aggressive growth of lung metastatic tumor cells. To avoid this phenomenon, the mice injected with src-transformed cells were sacrificed and autopsied for metastases at the 2nd week. Metastasized lung nodules were counted after insufflation of lung with 15% Indian ink (Wexler H., J. Natl. Cancer Inst. 36:641–645, 1966).

In some experiments, BALB/c mice of wild type or with suppressed natural killer (NK) cells were used. To eliminate NK activity, 200 $\mu$l of the anti-asialo $GM_1$ serum was injected into the tail vein of 7–8 week-old BALB/c mice for 3 days prior to injection of tumor cells. The anti-asialo $GM_1$ serum is known to specifically bind to NK cells to suppress their function (Kasai M. et al., Eur. J. Immunol. 10:175–180, 1980).

The results of tumorigenicity and invasive/metastatic potential obtained from A31-1-1 cells and A31-1-13 cells are shown in the following Table 1.

TABLE 1

Metastasis Assay in A31-1-1 and A31-1-13 Cells Transformed with UV, MCA and Ki-MSV

| Cell line | No. of mice given injections | No. of nodules | No. of mice with nodules (nodules/mouse) |
| --- | --- | --- | --- |
| Cells Transformed by UV* | | | |
| 1-1UV | 5† | 0 | 0 |
| 1-13UV | 5† | 0 | 0 |
| Cells Transformed by MCA* | | | |
| 1-1MCA | 5† | 0 | 0 |
| 1-13MCA | 5† | 0 | 0 |
| Cells Transformed by Ki-MSV* | | | |
| 1-1ki-msv1 | 5† | 0 | 0 |
| 1-1ki-msv2 | 5† | 0 | 0 |
| 1-1ki-msv3 | 5† | 0 | 0 |
| 1-1ki-msv4 | 5† | 0 | 0 |
| 1-1ki-msv5 | 5† | 0 | 0 |
| 1-13ki-msv1 | 5† | 0 | 0 |
| 1-13ki-msv2 | 5† | 0 | 0 |
| 1-13ki-msv3 | 5† | 0 | 0 |
| 1-13ki-msv4 | 5† | 0 | 0 |
| 1-13ki-msv5 | 5† | 0 | 0 |
| Positive Control fos-SR-3Y1-202 | 3‡ | 324 | 3 (149,103,72) |
| Negative Control 3Y1 | 5† | 0 | 0 |

*All of transformants were tumorigenic when $10^6$ cells of each line were subcutaneously injected into BALB/c nude mice.
†$5 \times 10^5$ cells of each line were intravenously injected into the tail vein of BALB/c nude mice. After 5 weeks, the animals were sacrificed and autopsied for lung metastasis.
‡The animals were autopsied at 2 weeks.

As shown from Table 1, no lung invasive/metastatic potential was observed in transformed cells. When rat 3Y1 cells transformed with v-src and v-fos (fos-SR-3Y1-202) were injected as a positive control, a number of metastatic lesions were found in lung.

Thus, BALB/c 3T3 A31 variant cells, A31-1-1 and A31-1-13, were found to be susceptible to neoplastic transformation by different kinds of carcinogens such as UV irradiation, chemicals and ras oncogenes. Although the transformants were tumorigenic, their invasive/metastatic potentials examined by experimental invasion/metastasis assay were negligible.

Example 2

Transfer of the Activated c-Ha-ras Oncogene into BALB/c 3T3 A31 Variant Cells

To isolate cells expressing an activated Ras oncoprotein at a high level, A31-1-1 and A31-1-13 were transformed by introducing a plasmid containing the activated c-Ha-ras (derived from T24 bladder carcinoma cells) and a selectable marker neo (pSV2neo-ras). Transformation was performed by electroporation (Tatsuka M., et al., Exp. Cell Res. 178:154–162, 1988). The transformants were selected in the presence of 400 and 1000 $\mu$g/ml of G418. Two clones, 1-1 ras and 1-13 ras, were isolated in the presence of 400 µg/ml of G418 and other two clones, 1-1ras1000 and 1-13ras1000, were isolated in the presence of 1000 µg/ml of G418. All the isolated clones had similar properties to those shown by cells transformed with v-Ki-ras. These cells were used for the following experiments.

Southern Blot Analysis of Incorporated Gene

Genomic DNA from each ras-transformed cell was digested with the restriction enzyme SacI and transferred to a nitrocellulose membrane by using the BIO-DOT SF apparatus (Bio-Rad). The membrane was hybridized with the $^{32}$P-labeled ras probe and detected on X-ray film. The copy number of the introduced gene was determined by densitometry. As a result, the ras gene introduced into cells was detected as a 3.0-kb SacI band.

Northern Blot Analysis of Transcribed mRNA

Cytoplasmic RNA was prepared by guanidinium thiocyanate-chloroform extraction (Chomczynski P. et al., Anal. Biochem. 162:648–657, 1977). Blotting and hybridization were performed as described by Maniatis et al. (Maniatis T. et al., Molecular Cloning: A Laboratory Manual, Cold Spring Harbor Laboratory, New York, 1982). The introduced c-Ha-ras and v-src genes were assayed for mRNA using each $^{32}$P-labeled specific probe. As a result, mRNA of ras was detected.

This confirmed that the ras gene had been integrated into the gene of cells and transcribed into mRNA.

Evaluation of the Copy Number of ras by Slot Blot Analysis

Each 5, 10 or 15 µg of genomic DNA digested with SacI was hybridized with the $^{32}$P-labeled SacI/SacI fragment of the c-Ha-ras gene derived from T24 human bladder carcinoma by slot blotting. The results are shown in FIG. 1. The copy number was higher in 1-1ras1000 and 1-13ras1000 cells than in the cells selected in the presence of 400 µg/ml of G418 (16- and 4-times, respectively).

Immunoblotting Analysis of p21$^{ras}$

The expression level of Ras oncoprotein was examined by immunoblotting using an anti-p21$^{ras}$ monoclonal antibody.

Pelleted cells were lysed in Laemmli's sample buffer (Laemmli U. K., Nature 227:680–685, 1979) by a brief sonication. The protein concentration was adjusted to 2 mg/ml. The lysates were heated at 100° C. for 3 min, and loaded onto a 15% polyacrylamide gel. Proteins in the gel were electroblotted onto Durapore filters (Towbin H. et al., Proc. Natl. Acad. Sci. USA 76:4350–4354, 1979) and incubated for 18 h with an anti-p21$^{ras}$ monoclonal antibody, NCC-RAS-004 (Kanai T. et al., Jpn. Cancer Res. 78:1314–1318, 1987). This antibody can detect the p21$^{ras}$ protein transcribed by the c-Ha-ras gene with a point mutation at the codon 12. During then, specific binding on membranes was blocked with skimmed milk. The proteins transferred on the membranes were further incubated with $^{125}$I-labeled Protein G (Akerstrom B. et al., J. Immunol. 135:2589–2592, 1984) for 1.5 h, then autoradiographed on Fuji RX X-ray film.

The results are shown in FIG. 2. A rapidly migrating weak band corresponds to the endogenous p21$^{ras}$. A slowly migrating band of the p21$^{ras}$ oncoprotein translated from the mutated c-Ha-ras gene (Taparowski E. et al., Nature 300:762–765, 1982) was detected specifically in the ras-transformed cells. Such a slowly migrating band of the p21$^{ras}$ oncoprotein was never detected even when 10-fold excess (50 µl) of the parental cell lysate was electrophoresed on the gel (FIG. 2).

Evaluation of Tumorigenicity and Invasive or Metastatic Potential of the Cells Transformed with c-Ha-ras and v-src To examine whether or not an increased expression level of the p21$^{ras}$ oncoprotein affects the invasive/metastatic potential of transformants, the cells transformed with c-Ha-ras and v-src were tested for their tumorigenicity and invasive/metastatic potential. The results are shown in the following Table 2.

TABLE 2

Tumorigenicity and Invasive or metastatic Potential in A31-1-1 and A31-1-13 Cells Transformed with c-Ha-ras and v-src Oncogenes

| | Tumorigenicity | | Metastatic potential | |
|---|---|---|---|---|
| Cell line | No. of tumor bearing mice/No. of injected mice | No. of mice given injections | No. of nodules | No. of mice with nodules (nodules/mouse) |
| Parental Variant Cells or Cells Transfected with Empty Vector | | | | |
| 1-1 | 0/5* | 5‡ | 0 | 0 |
| 1-13 | 0/5 | 5‡ | 0 | 0 |
| 1-1neo | ND | 3‡ | 0 | 0 |
| 1-13neo | ND | 3‡ | 0 | 0 |
| Cells Transfected with Mutated c-Ha-ras1 Oncogene | | | | |
| 1-1ras4 | 3/3† | 5‡ | 0 | 0 |
| 1-1ras1000 | 3/3† | 5‡ | 0 | 0 |
| 1-13ras2 | 3/3† | 5‡ | 0 | 0 |
| 1-13ras1000 | 3/3† | 5‡ | 0 | 0 |
| Cells Transfected with v-src Oncogene | | | | |
| 1-1src, pooled cells | 313† | 3§ | 154 | 3 (58,48,48) |
| 1-1src,clone1 | ND | 3§ | 286 | 3 (126,89,71) |
| 1-1src,clone2 | ND | 3§ | 213 | 3 (94,67,52) |
| 1-1src,clone3 | ND | 3§ | 316 | 3 (118,116,82) |
| 1-13src, pooled cells | 3/3† | 3§ | 172 | 3 (69,53,50) |
| 1-13src, clone1 | ND | 3§ | 203 | 3 (85,77,41) |
| 1-13src, clone2 | ND | 3§ | 342 | 3 (134,105,103) |
| 1-13src, clone3 | ND | 3§ | 265 | 3 (104,92,69) |
| Additional Transfection with v-src Oncogene or Empty Vector to 1-1ras1000 Cells | | | | |
| 1-1ras1000hyg | 3/3† | 6‡ | 0 | 0 |
| 1-1ras1000src | 3/3† | 9§ | 1227 | 9(196,165,146, 138,130,124 116,112,100) |

*Mice injected subcutaneously with 1 × 10$^6$ of each cell variant were tumor-free up to 10 weeks after injection.
†Cells from ras-and src-transfectants gave rise to tumors within 1–2 weeks. In all of injected animals, tumor weight was 9–10 g after 3 weeks.
‡The animals were autopsied at 5 weeks.
§The animals were autopsied at 2 weeks.

As shown from Table 2, the increased expression level of the p21$^{ras}$ oncoprotein did not affect at all the invasive/metastatic potential of transformants.

This revealed that the invasive/metastatic phenotype of the ras-transformed cells was very stable and was hardly changed during in vitro cultivation.

Example 3
Invasive or Metastatic Potential of BALB/c 3T3 Variant Cells can be Induced by a Viral Oncogene v-src A viral oncogene, v-src, has a strong transforming activity and can induce invasive/metastatic potential simultaneously, depending on the type of the recipient cell. Thus, the effect of v-Src oncoprotein on the parental BALB/c 3T3 A31 variant cells as well as on the ras-transformed cells was examined by the transfection with this oncogene.

Upon transfection with v-src, the parental cells (BALB/c 3T3 A31 cells) formed foci in vitro, indicating that the v-src gene itself has the activity of transforming cells. The shape of the focus-forming transformed parental cells was not so different from that of the cells transformed with the mutated ras gene.

Then, the transformants were confirmed to contain the transfected v-src gene as a 2.9-kb EcoRI fragment by Southern blotting and a functional expression of v-Src oncoprotein was also confirmed as follows.

Immunoblotting Analysis and Tyrosine Kinase Assay of p60$^{src}$

The expression level of v-src gene products in src-transformants were examined by immunoblotting analysis of p60$^{src}$ using anti-p60$^{src}$ serum specific to Src protein (Cooper J. A. et al., J. Virol. 48:752–764, 1983). The src-transformants were also examined for phosphorylation of Src protein by the kination assay as described by Jove et al. (Jove R. et al., J. Virol. 60:849–857, 1986).

As a result, it was difficult to distinguish v-Src from the endogenous c-Src by immunoblotting analysis (FIG. 3A). However, an enhanced autophosphorylation of the p60$^{src}$ was observed in the transformed cells by kination assay following immunoprecipitation experiment (using anti-p60$^{src}$ serum) (FIG. 3B).

src-Transformed Cells Have Acquired Tumorigenicity and Invasive or Metastatic Potential A pooled fraction of the src-transformed cells derived from A31-1-1 and A31-1-13 efficiently formed tumors within 1–2 weeks after injection, and the latency period was the same as that of the ras-transformed cells. The pooled transformants and each transformed clone (1-1src clones 1 to 3, 1-13src clones 1 to 3, and 1-1ras1000src) formed a number of lung metastases by the experimental invasion/metastasis assay (Table 2).

Figure 4:
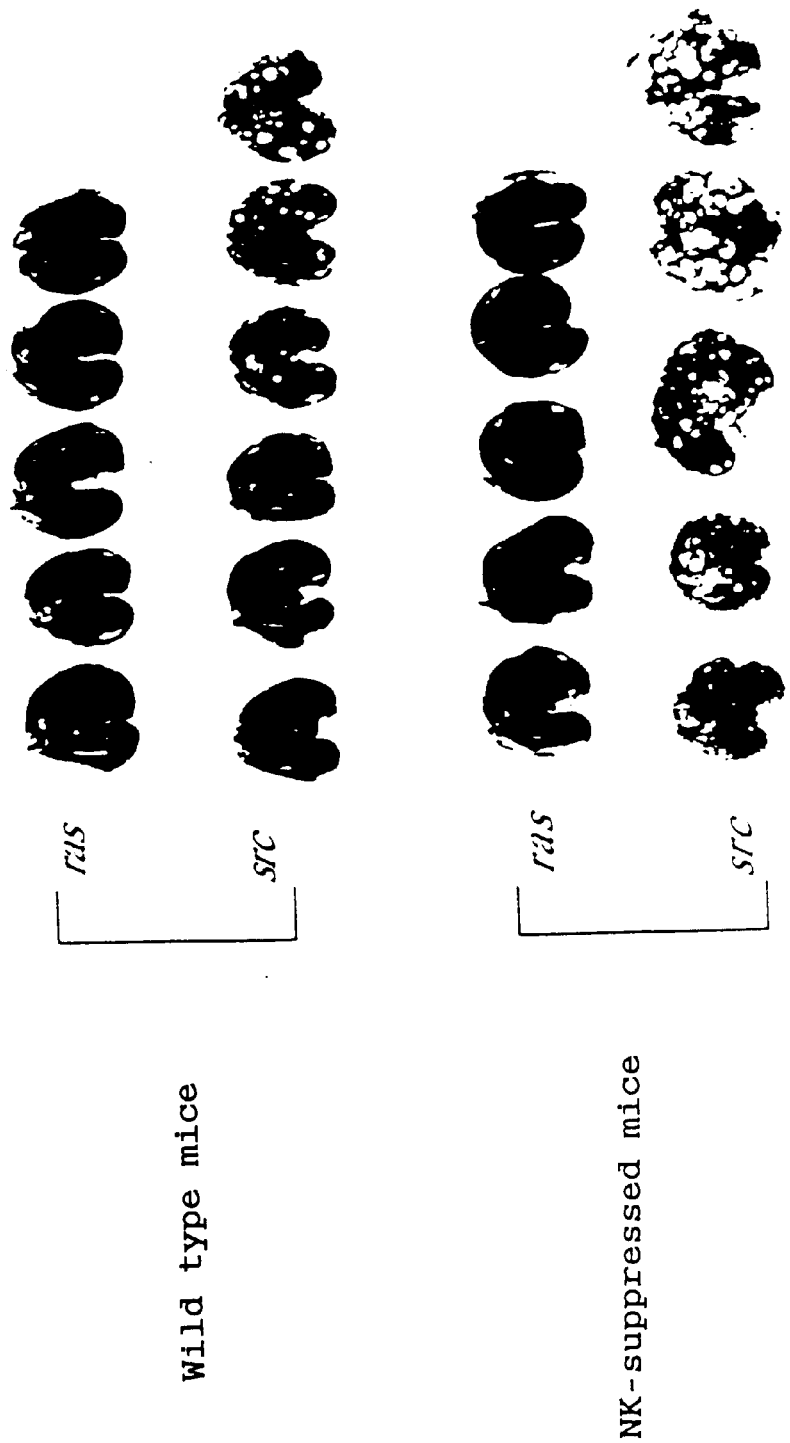
FIG. 4. Invasive or metastatic potentials of ras-transformed 1-1ras1000 and src-transformed 1-1src cells in either wild-type or NK-suppressed BALB/c mice (morphologic photographs the organisms).

Thus, a clear difference was observed between the activated ras- and v-src-transformed cells in their invasive/metastatic potential analyzed by the experimental invasion/metastasis assay. In order to examine whether or not this difference results from the sensitivity of the ras-transformed cells to nude mice, metastatic potentials of the ras-transformed 1-1ras1000 cells and src-transformed 1-1 src cells were compared using wild-type and NK-suppressed BALB/c mice instead of nude mice. This yielded the same results in either wild-type or NK-suppressed mice (FIG. 4), indicating that the above difference in metastatic potential is not due to the sensitivity to NK activity in nude mice.

Example 4

In vitro Invasiveness and Cell Motility of the ras- and src-Transformed Cells

Figure 5:
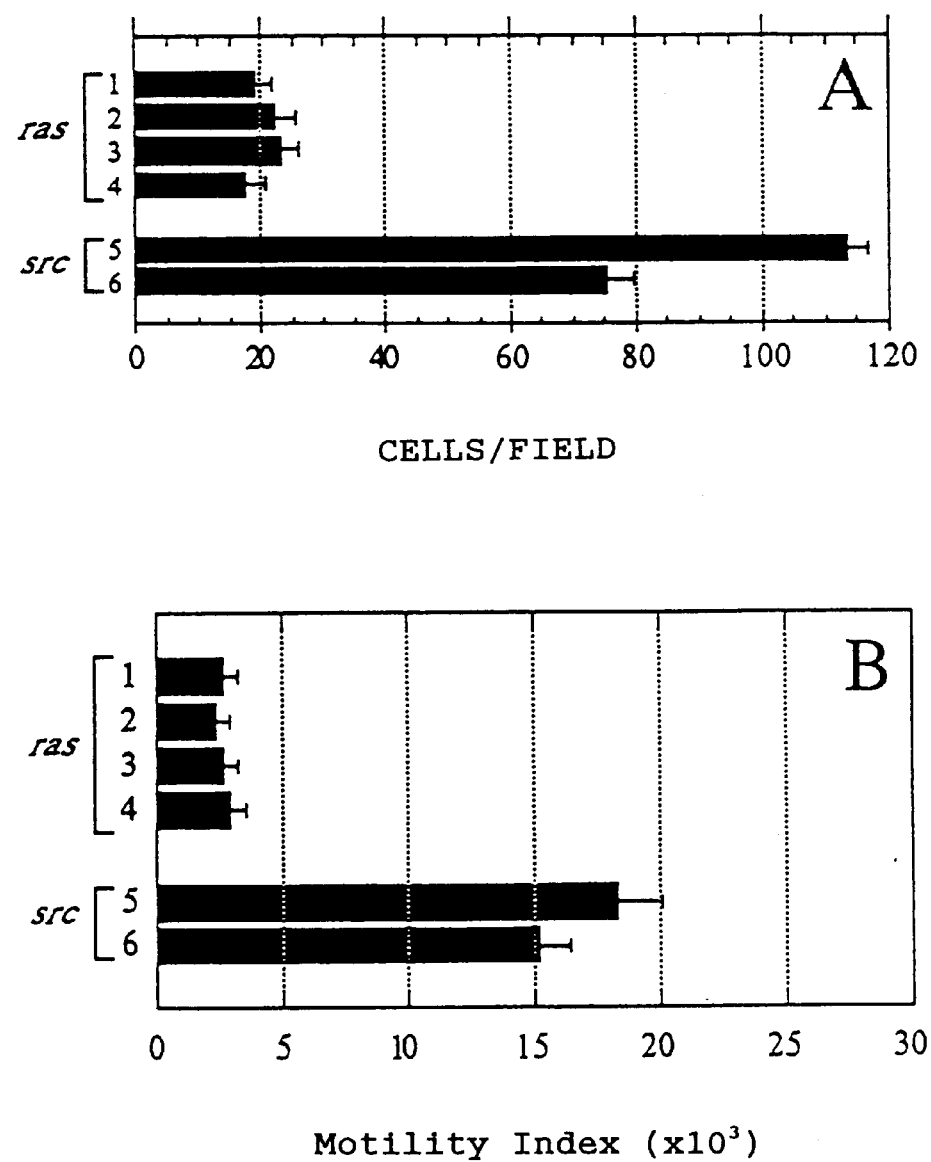
FIG. 5. (Parts A–B) In vitro invasion assayed by counting the number of cells penetrating MATRIGEL-coated filters using a microscope of 400 magnifications (A), and cell motility as the motility index measured by computer-aided digital image analysis (B). Each column indicates the mean of triplicate samples with standard deviation. Column 1:1-ras; Column 2: 1-1ras1000; Column 3:1-13ras; Column 4:1-13ras1000; Column 5:1-1src; Column 6:1-13src.

In vitro cell motility and invasiveness are known to be closely related to the invasive/metastatic potential of tumor cells. An invasive ability of cells was analyzed by the method of Albini et al. (Albini A. et al., Cancer Res. 47:3239–3245, 1987) using a modified Boyden chamber fitted with a MATRIGEL-coated filter. As a result, v-src transformed cells A31-1-1 and A31-1-13 showed invasion indices 4–5 times higher than those of the ras-transformed cells (FIG. 5A). The invasiveness was not affected by an increased expression level of the mutated Ras oncoprotein.

Cell motility was measured on MATRIGEL-coated dishes using computer-aided digital image analysis (Tatsuka M. et al., Exp. Cell Res. 185:342–352, 1989) and indicated by the motility index. As a result, the motility indices of the src-transformed cells were also 6–7 times higher than those of the ras-transformed cells (FIG. 5B). This suggests that v-Src oncoprotein induces various additional cellular phenotypes that are not induced by the activated Ras protein, and consequently the src-transformants become invasive/metastatic.

Example 5

Induction of Metastatic Potential by DNA Derived from Human Tumor Cells

DNA extracted from various human metastatic tumor cells was transfected into non-metastatic 1-1ras1000 cells to examine induction of metastatic potential.

A. Experimental Procedures (1) Extraction of DNA

The following human tumor cell lines were used as experimental materials to extract whole genomic DNA according to the method of Maniatis et al. (Maniatis, T. et al., Molecular Cloning: A Laboratory Manual, Cold Spring Harbor Laboratory, New York, 1982).

A204 (ATCC HTB-82): rhabdomyosarcoma;

Malme-3M (ATCC HTB-64): lung-metastasized malignant melanoma;

Mewo (JCRB0066): malignant melanoma;

SW480 (ATCC CCL-228): colon adenocarcinoma.

These cells were obtained from American Type Culture Collection (ATCC) or Japanese Collection of Research Biosources (JCRB).

The size of each DNA extracted from these cell lines exceeded 20–90 kb, as determined by pulsed field electrophoresis.

(2) DNA Transfection

DNA transfection was performed by the calcium phosphate method (Graham, F. L. and Van Der EB, A. J., Transformation of rat cells by DNA of human adenoma 5, Virology, 54:536–539, 1973). Prior to transfection, 5×10$^5$ 1-1ras1000 cells were seeded in dishes of 100 mm in diameter. Each genomic DNA sample prepared by mixing 1 mg of genomic DNA with 100 µg of pSV2gptDNA (dominant selectable marker) was precipitated and added in 20 dishes. After 4 hours, cells were shocked with 15% glycerol for 60 sec. Cells were grown for 16 h in Eagle's MEM supplemented with 10% fetal bovine serum. Then, a selective medium containing xanthine (250 µg/ml), hypoxanthine (15 µg/ml), thymidine (10 µg/ml), aminopterin (2 µg/ml) and mycophenolic acid (MPA: 25 µg/ml) was added to each dish. MPA-resistant colonies which appeared on dishes were pooled for further experiments.

(3) Evaluation of Metastatic Potential

Male BALB/c nude mice were obtained at 6–7 weeks of age. MPA-resistant cells were collected by trypisinization. The pooled cells from each transfection were washed with Hanks' solution and 5×10$^5$ cells were injected into the tail vein of 7–8 week-old nude mice. The animals were sacrificed after 5 weeks and autopsied. Cells were obtained by culture of minced lung. If a metastatic lesion was formed in lung, a colony appeared upon culture on an MPA-selective medium. Normally, a colony was generated from each focus metastasized to the lung of one mouse. The number of colonies was counted and all the colonies from each mouse were used for a second round of transfection.

B. Results

MPA-resistant colonies incorporating DNA from the cell line A204, Malme-3M, Mewo or Sw480 metastasized to lung (Table 3). MPA-resistant colonies recovered from the lung with metastases were pooled and cultured, and then reinjected into mice. As a result, all the colonies metastasized to lung (Table 3).

A pooled strain of 1-1ras1000 cells incorporating DNA of SW480 was used for further transfection experiments. When DNA extracted from this strain was retransfected into 1-1ras1000 (second transfection), those cells metastasized to lung. When the same procedure was repeated again (third transfection), lung metastasis was observed. The number of colonies metastasized to lung increased with an increase of rounds of transfection (Table 3). Transformed cells were stable with no change in metastatic potential after at least 5 passages in normal medium.

TABLE 3

| DNA tranfected | No. of mice given i.v. administration | No. of colonies observed per mouse |
|---|---|---|
| First transfection | | |
| 1-1ras1000 | 5 | 0,0,0,0,0 |
| A204 | 5 | 3,4,12,15,18[1] |
| Malme-3M | 5 | 0,5,6,8,9[2] |
| Mewo | 5 | 0,0,0,1,2[3] |
| SW480 | 5 | 0,3,5,6,8[4] |
| Second transfection | | |
| 1-1ras1000 | 6 | 0,0,0,0,0,1 |
| 1-1ras1000 SW480-T1 | 6 | 15,20,24,34,48,63[5] |
| Third transfection | | |
| 1-1ras1000 | 4 | 0,0,0,0 |
| 1-1ras1000 SW480-T2 | 4 | 23, >200, >200, >200 |

[1]Metastasis occurred when $10^5$ cells recovered from 18 colonies were reinjected into the tail vein of nude mice.
[2]Metastasis occurred when $10^5$ cells recovered from 9 colonies were reinjected into the tail vein of nude mice.
[3]Metastasis occurred when $10^5$ cells recovered from 2 colonies were reinjected into the tail vein of nude mice.
[4]Cells recovered from 8 colonies (1-1ras1000 SW480-T1) were used for a second round of transfection.
[5]Cells recovered from 63 colonies (1-1ras1000 SW480-T2) were used for a third round of transfection.

What is claimed is:

1. A tumor cell obtained by transfecting a BALB/c 3T3 A31 cell with an oncogene of the ras family, wherein said cell has tumorigenic potential but lacks invasive or metastatic potential, and wherein said tumorigenic potential and said lack of invasive or metastatic potential have been conferred by introduction of the oncogene of the ras family, and without co-transfecting with another oncogene.

2. The tumor cell according to claim 1, wherein the oncogene of the ras family is the c-Ha-ras gene.

3. The tumor cell according to claim 1, which is 1-1 ras 1000 (accession number FERM BP-5406).

4. A method for preparing the tumor cell according to claim 1, comprising providing a BALB/c 3T3 A31 clone; and introducing an oncogene of the ras family into said BALB/c 3T3 A31 clone.

5. The tumor cell according to claim 1, which is a BALB/c 3T3 A31-1-1 or a BALB/c 3T3 A31-1-13 cell.

6. The tumor cell of claim 1, wherein said oncogene is an activated oncogene.

7. The tumor cell of claim 1, wherein said oncogene is an activated c-Ha-ras.

8. The method according to claim 4, wherein the BALB/c 3T3 A31 clone is BALB/c 3T3 A31-1-1 or BALB/c 3T3 A31-1-13.

9. The method according to claim 4, wherein the oncogene of the ras family is the c-Ha-ras gene.

10. The method according to claim 4, wherein the tumor cell is 1-1 ras 1000 (Accession No. FERM BP-5406).

11. A screening method for genes having the property of conferring invasive or metastatic potential, which comprises transfecting DNA of a tumor tissue obtained from the surface or inside of a mammal or of a tumor cell line into a tumor cell having tumorigenic potential but lacking invasive or metastatic potential, isolating cells having acquired invasive or metastatic potential and extracting DNA therefrom, wherein said tumor cell is obtained from a BALB/c 3T3 A31 cell and wherein said tumorigenic potential has been conferred by an oncogene of the ras family.

12. The method according to claim 11, wherein the DNA is a genomic gene of a metastatic tumor cell or a cDNA library prepared with a mammalian cell expression vector.

13. The method according to claim 12, wherein the tumor cell transfected with DNA is 1-1 ras 1000 (Accession No. FERM BP-5406).

14. A tumor cell obtained from a BALB/c 3T3 A31 cell transfected with an oncogene of the ras family and a src oncogene, wherein said cell has tumorigenic potential and invasive or metastatic potential.

* * * * *